United States Patent [19]
Erickson et al.

[11] Patent Number: 5,664,580
[45] Date of Patent: Sep. 9, 1997

[54] GUIDEWIRE HAVING BIMETALLIC COIL

[75] Inventors: David S. Erickson, Stillwater; Rudy Mazzocchi, Dellwood, both of Minn.

[73] Assignee: Microvena Corporation, White Bear Lake, Minn.

[21] Appl. No.: 381,517

[22] Filed: Jan. 31, 1995

[51] Int. Cl.$^6$ ............................................. A61B 5/00
[52] U.S. Cl. .................................................. 128/772
[58] Field of Search .............................. 128/657, 772; 604/95, 164, 280–282

[56] References Cited

U.S. PATENT DOCUMENTS

| | | |
|---|---|---|
| 3,789,841 | 2/1974 | Antoshkiw . |
| 3,941,119 | 3/1976 | Corrales . |
| 4,003,369 | 1/1977 | Heilman et al. . |
| 4,020,829 | 5/1977 | Willson et al. . |
| 4,538,622 | 9/1985 | Sanson et al. ............... 128/772 |
| 4,619,274 | 10/1986 | Morrison ...................... 128/772 |
| 4,721,117 | 1/1988 | Mar et al. ..................... 128/772 |
| 4,748,986 | 6/1988 | Morrison et al. ............ 128/772 |
| 4,757,827 | 7/1988 | Buchbinder et al. ........ 128/772 |
| 4,763,747 | 8/1988 | Gambale ....................... 128/657 |
| 4,811,743 | 3/1989 | Stevens ........................ 128/772 |
| 4,884,579 | 12/1989 | Engelson ..................... 128/772 |
| 4,922,924 | 5/1990 | Gambale et al. ............. 128/772 |
| 4,971,490 | 11/1990 | Hawkins ...................... 128/772 |
| 5,007,434 | 4/1991 | Doyle et al. ................. 128/772 |
| 5,050,660 | 9/1991 | Gambale et al. ............. 128/772 |
| 5,063,935 | 11/1991 | Gambale ...................... 128/657 |
| 5,067,489 | 11/1991 | Lind ............................. 128/772 |
| 5,069,217 | 12/1991 | Fleischhacker, Jr. ........ 128/657 |
| 5,095,915 | 3/1992 | Engelson ...................... 128/772 |
| 5,129,890 | 7/1992 | Bates et al. ................... 604/281 |
| 5,144,959 | 9/1992 | Gambale et al. .............. 128/772 |
| 5,147,317 | 9/1992 | Shank et al. .................. 604/164 |
| 5,174,302 | 12/1992 | Palmer .......................... 128/772 |
| 5,176,149 | 1/1993 | Grenouillet ................... 128/772 |
| 5,243,996 | 9/1993 | Hall .............................. 128/772 |
| 5,253,653 | 10/1993 | Daigle et al. ................. 128/772 |
| 5,520,194 | 5/1996 | Miyata et al. ................ 128/772 |

FOREIGN PATENT DOCUMENTS 0014424  6/1980  European Pat. Off. .

OTHER PUBLICATIONS

Schematic diagrams of two guidewires which applicant believes were commercially available on Jan. 30, 1994.
Pages from ACS product literature dated in 1988.

*Primary Examiner*—Max Hindenburg
*Attorney, Agent, or Firm*—Fredrikson & Byron

[57] ABSTRACT

The present invention provides a coil having at least distal and proximal coil segments, one of the segments being more radiopaque than at least one of the other segments. The guidewire includes an elongate wire which desirably extends along substantially the entire length of the coil and continues proximally of the coil. In a 2-segment coil, the distal end of the distal coil segment is attached to the wire, the proximal end of the distal segment is attached to the distal end of the proximal coil, and the proximal end of the proximal coil segment is attached to the wire. Otherwise, the coil floats freely with respect to the wire between the coil's distal and proximal ends. A method of making such a guidewire is also disclosed.

17 Claims, 3 Drawing Sheets

GUIDEWIRE HAVING BIMETALLIC COIL

FIELD OF THE INVENTION

The present invention generally relates to medical guidewires, and specifically provides a medical guidewire useful in the context of radiographic procedures.

BACKGROUND OF THE INVENTION

Many non-invasive or minimally invasive medical procedures employ medical guidewires to direct a catheter or a mechanical medical device to a desired treatment site within a patient's vascular system or the like. When performing such procedures, the operator typically views the progress of the guidewire within the patient's body by means of a fluoroscope or other radiographic instrument. By watching the guidewire on the monitor and manipulating the proximal portion of the guidewire outside the patient's body, the operator can guide the distal portion of the guidewire to a position adjacent the treatment site. Once properly positioned, a catheter or other treatment device, e.g. an atherectomy device, can be guided over a portion of the guidewire and the desired treatment can be performed.

Some materials are more radiopaque than others, with the more radiopaque materials being easier to see on the monitor than the less radiopaque materials. The majority of the guidewires commercially available are made of stainless steel or other metals having a similar radiopacity. Stainless steel is not very radiopaque at smaller diameters, though, and most stainless steel guidewires below about 0.032 inches in diameter are provided with a radiopaque area adjacent the distal end to make the distal end of the guidewire more visible for deployment. This radiopaque area may take the form of radiopaque marking bands, for example, which typically are small rings of a more radiopaque material such as gold, platinum or tungsten, attached to the guidewire.

Many guidewires include a helically wound coil carried over a distal segment of the guidewire to increase flexibility of the distal tip. A core wire usually extends along the length of the lumen of the coil and a bead is provided at the end of the guidewire. The bead is attached to both the core and the coil to lock them together at the distal end. This will help prevent a segment of the guidewire from being lost in the patient's body if the coil or core breaks and also help transmit torque to the coil when the proximal part of the guidewire is turned by the operator to steer the guidewire.

Some guidewires use integrally formed core wires which extend throughout the entire length of the coil and are either bonded to or integrally formed with a bead on the distal end. Other guidewires include a "safety wire" which is bonded to the distal tip of the main wire of the guidewire, which terminates within the lumen of the coil, and the safety wire extends distally to be bonded to a bead at the distal end of the coil. In guidewires which use safety wires, the safety wire must be securely bonded to the core wire, typically by means of a solder or braze joint.

One way which has been used to make stainless steel guidewires more visible is to make the helical coil adjacent the distal end of the guidewire more radiopaque. This may be accomplished by forming the coil from wire of a radiopaque material or by coating the coil with a relatively thick coating of a radiopaque material, such as coating the coil with gold or platinum. Since radiopacity is tied, at least in part, to density, it is generally easier to see a coil which is formed entirely of a radiopaque material than it is to see a coil coated with the radiopaque material.

Although making a coil carried over a distal portion of the guidewire from a radiopaque material makes it easier to steer the guidewire because it is easier to see, this increased visibility can interfere with visualization of the patient's tissues to be treated. Some tissues being treated by the operator tend to show up fairly poorly on the monitor. Other tissues to be treated, such as a calcified atheroma in a patient's vessels, tend to be fairly radiodense. When a solid, radiopaque length of the guidewire is positioned in the same area of the monitor view as the tissue to be treated, it can frequently be very difficult to see the tissue adjacent to or surrounding the guidewire—if the tissue is not very radiodense the guidewire can essentially mask the treatment site, while if the tissue is more radiodense it can be hard to distinguish the guidewire from the tissue, making it difficult to locate the margins of the treatment site.

Some have proposed solving this problem by making the helical coil of the guidewire of two different materials. For example, U.S. Pat. No. 4,538,622 (Samson et al.) shows such a two-material design. In such designs, a distal segment of the coil is formed of a strong radiopaque material, such as gold or platinum, and the rest of the coil is formed of a less radiopaque material, such as stainless steel.

Such a guidewire design permits the operator to easily see the distal coil length during deployment of the guidewire. The guidewire is urged past the treatment site so that the distal coil segment is positioned beyond the tissue to be treated. This positions the less radiopaque proximal coil segment adjacent the treatment site, permitting the operator to see the tissue at the treatment site with minimal interference in visibility from the guidewire itself.

Although such two-material coils do have certain advantages, they tend to be more difficult to steer into position than some other guidewires. Such guidewires can also present problems in tracking a catheter or other treatment device along the guidewire adjacent the junction between the proximal and distal coil segments. The distal and proximal coil segments typically must be bonded to one another and to the core wire extending through the lumen of the coil to provide a sure connection and to ensure that torque of the proximal segment of the guidewire is transmitted to the coil to steer the distal segment of the wire.

Samson's soldered design can make it difficult to steer the wire through a patient's vascular system. This problem is particularly acute when the guidewire is used in narrowing vessels, such as vessels which are narrowed by atheroma. In Samson's design, if movement of the coil is restricted, such as when the coil is in contact with atheroma, the friction of the coil against the patient's tissue can make it very difficult, if not impossible, to turn the tip of the guidewire to steer it beyond the narrowing of the vessel because the intermediate solder bond to the coil prevents, or at least greatly restricts, relative movement between the core wire and the coil.

The junction between the three elements (or four elements, if a safety wire is used) of Samson's design yields a stiff, hard length of the guidewire which can often be a centimeter or longer. It has been found that sharp discontinuities in flexibility, however, tend to cause the guidewire to bend unevenly during deployment, which can make the guidewire more difficult to steer. When a catheter or other device is urged forwardly over the guidewire for treatment, it will follow, or "track", the guidewire into the treatment position. If the guidewire defines fairly smooth, continuous curves as it bends, it will be fairly easy for catheters to track the guidewire. When the guidewire has relatively sharp discontinuities in flexibility, this will interrupt the otherwise smooth flow of a curve, making it more difficult to track a catheter or the like over the guidewire.

Accordingly, two-material coils such as those proposed by Samson et al. are useful in providing enhanced visibility for deployment without significantly interfering with an operator's ability to see a patient's tissue during treatment. However, these designs are inherently flawed in that they tend to produce sharp discontinuities in flexibility, making it more difficult to steer the guidewire into place and to deploy the treatment device.

SUMMARY OF THE INVENTION

The present invention provides a guidewire having a coil comprising at least a distal coil segment and a proximal coil segment, one of the coil segments being more radiopaque than at least one of the other coil segments. The guidewire includes an elongate wire which extends within the lumen of the coil, desirably extending along substantially the entire length of the coil and proximally beyond the proximal end of the coil. In a two-segment coil, the distal end of the distal coil segment is attached to the wire and the proximal end of the distal coil segment is attached to the distal end of the proximal coil segment while the proximal end of the proximal coil segment is attached to the wire. These are the only bonds between the distal coil segment, the proximal coil segment and the core wire, permitting the core to float freely within the lumen of the coil.

The free-floating core of the invention enhances the flexibility of the portion of the guidewire including the coil by allowing the core to move with respect to the coil. Also, eliminating the additional bond between the proximal end of the distal coil segment, the distal end of the proximal coil segment and the core wire avoids the sharp discontinuities in flexibility typifying prior art devices. Accordingly, a guidewire of the present invention will usually be easier to steer into position and permit better tracking of a catheter or the like than is possible with most prior art designs.

The present invention also contemplates a method of making such a guidewire. In accordance with this method, a guidewire having a core wire along a distal portion of its length is provided. The proximal end of a proximal coil segment is bonded to the core wire and the distal end of the proximal coil segment is laser spot-welded to a proximal end of a distal coil segment. The distal coil segment is formed of a more radiopaque material than is the proximal coil segment. The distal end of the distal coil segment is bonded to the core wire adjacent its distal end, such as by bonding both the distal end of the distal coil segment and the distal end of the coil to a distal bead. Laser spot welding has been found remarkably superior to other means of attaching the distal and proximal coil segments to one another and provides a better guidewire than such other methods.

DETAILED DESCRIPTION OF THE PREFERRED EMBODIMENTS

Figure 1:
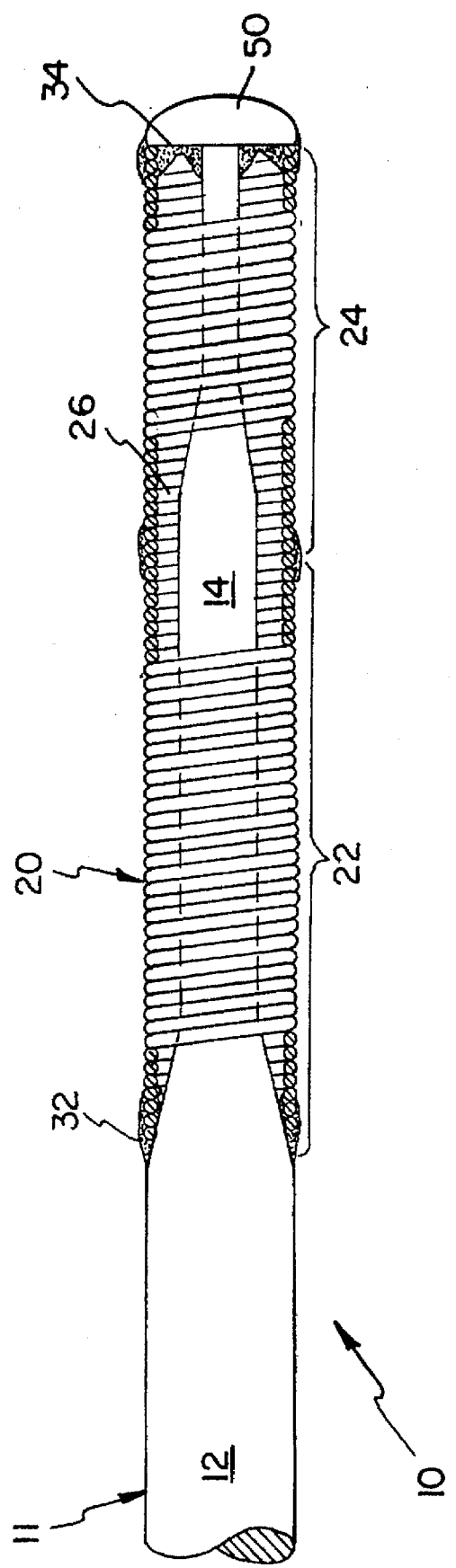
FIG. 1 is a side view in partial cross section of a guidewire in accordance with the present invention.
Figure 2:
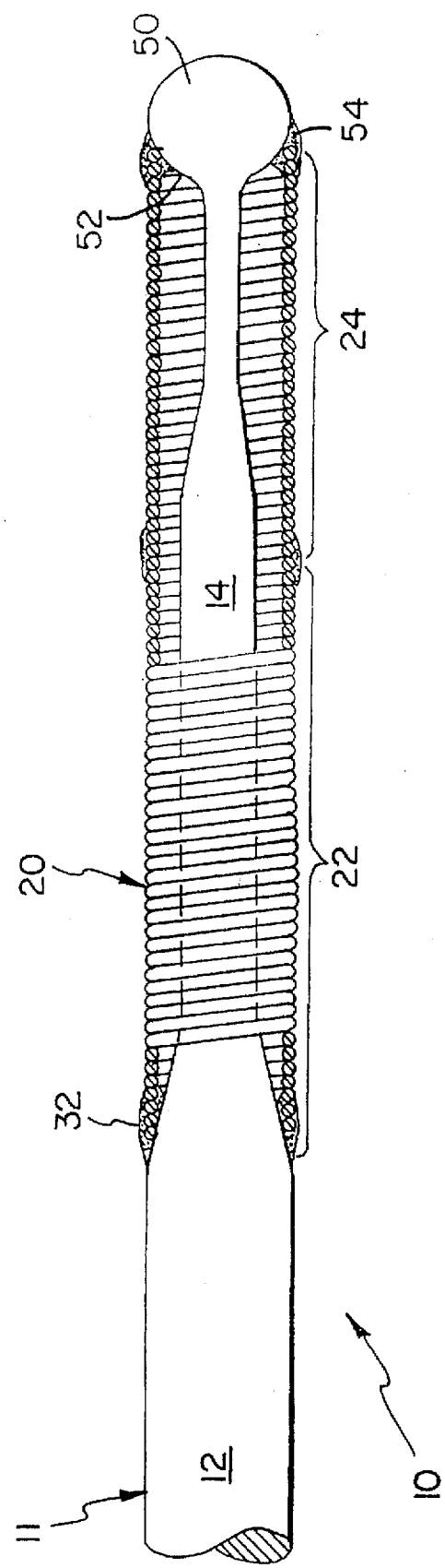
FIG. 2 is a side view in partial cross section of an alternative embodiment of a guidewire of the invention.

FIGS. 1 and 2 illustrate a guidewire 10 in accordance with the present invention. This guidewire includes a wire 11 having a proximal length 12 and a distal length 14. The overall length of the guidewire may vary from one application to another, depending in large part on the length of the path through which the guidewire will be expected to be guided. Typical lengths are on the order of about 145 cm to about 300 cm. The majority of the length of the coil will typically be in the proximal length, with the distal length being typically about 2–60 cm, depending on the application for which the wire will be used, with lengths on the order of 2–30 cm for being more common for non-cerebral applications and longer lengths usually being used primarily in cerebral applications.

While the proximal length can have a substantially constant diameter along its length, the distal length may taper from a diameter approximately equal to the diameter of the distal end of the proximal length down to a much smaller diameter adjacent the distal end of the guidewire. Such tapering designs are well known in the art and need not be discussed in length here. Briefly, though, the diameter of the distal length may taper substantially constantly along its length, or the change in diameter may take place in stages, with the changes between a length of a first diameter and a length of a second diameter being relatively gradual to define a taper between those lengths. Such a multi-taper core wire design is set forth in U.S. Pat. No. 4,538,622 (Samson et al.), the teachings of which are incorporated herein by reference. The diameter(s) of the distal length 14 of the wire may be the same as those set forth by Samson et al. or different, depending on the application for which the guidewire is intended.

In FIG. 1, the distal length terminates in an end which is attached to a separately formed bead 50 by means of an adhesive or a weldment, as described below. FIG. 2 illustrates an alternative embodiment wherein a retaining bead 50' is integrally formed at the distal end of the distal length. This bead may be formed, for example, by centerless grinding, as described in U.S. Pat. No. 5,067,489 (Lind), the teachings of which are incorporated herein by reference.

In an alternative embodiment (not shown), the distal length 14 of the wire 11 terminates proximally of the distal end of the guidewire 10. A safety wire (not shown) can be bonded to the wire 11 and extend distally beyond the end of the wire 11 to the distal end of the guidewire, where it is bonded to the cap 50, discussed below.

The wire 11 may be formed of any suitable material. For example, the wire may be formed of stainless steel (e.g, No. 304 stainless steel including about 20% chromium and about 10% nickel) or other like material. In a particularly preferred embodiment, however, the wire 11 is formed of a superelastic material. Such superelastic materials are known in the art of guidewires and the most common superelastic material for such applications is nitinol, a near-stoichiometric alloy of nickel and titanium, which may also contain some minor additions of other alloyed metals such as vanadium and chromium. The use of some such superelastic materials in medical guidewires is discussed at some length by Lind, incorporated by reference above.

Although a guidewire 10 having a wire 11 formed of stainless steel can readily benefit from the advantages of the present invention, superelastic materials such as nitinol are preferred due to a number of advantages inherent in superelastic materials. One advantage of nitinol is the superior flexibility of the wire, enabling the wire to be subjected to greater bending stresses without taking a permanent "set" or "kink". Nitinol also tends to have superior torsional properties, transmitting more of the torque applied by the operator to the proximal length of the guidewire extending outside of the patient's body to steer the guidewire. Particularly in light of the free-floating coil provided by the present invention and the reduced physical linkage between the coil and the wire, the improved torsion properties of nitinol can, in some instances, be necessary to permit the operator to easily steer the guidewire along a more tortuous path.

A coil 20 extends over the distal length 14 of the wire. Although the coil may extend over only a portion of that length or extend beyond the distal end of the wire, in the embodiment shown in FIG. 1, the coil begins adjacent the proximal end of the distal length and terminates at a position adjacent the distal end of the wire's distal length 14. In FIG. 2, the wire 11 is provided with an integrally formed bead 50', as noted above. The distal end of the coil in this embodiment desirably terminates adjacent the rearward shoulder 52 of the bead for bonding thereto, as explained below. The outer diameter of the coil is desirably substantially equal to the outer diameter of the proximal length 12 of the wire 10 and the coil defines a lumen 26 within which at least part of the distal length 12 of the wire is received.

The coil 20 is formed of two segments, a proximal segment 22 and a distal segment 24. Each of these coil segments is desirably formed of a wire twisted in a helical fashion to define a coil, as is standard in the art. These wires used to form the coil segments may have a diameter of, for example, about 0.002–0.006 inches (about 0.05–0.15 mm). The wire of the coil segments is desirably wound so that adjacent turns of the wire abut against one another, or so that the coil segments are "bottomed out". Although the overall length of the coil is desirably about the same as the length of the distal length 14 of the wire 11, a distal segment 24 of the coil on the order of about 1–3 cm, especially about 2 cm, has been found to work well. The length of the proximal segment 22 can be varied as desired to yield a coil 20 of an appropriate overall length.

The precise materials of which the wires comprising the two coil segments 22, 24 are formed is not critical, but it is important that the proximal segment be less radiopaque than the distal segment. In one preferred embodiment, the proximal coil segment is formed of a medical grade of stainless steel wire, e.g. a 304 V stainless steel, which has low radiopacity so that it is less visible on a fluoroscopic display.

The distal coil segment 24 is preferably formed of a material which is substantially opaque to X-rays and optimally has a density of at least about 13 gm/cm³. Such materials include gold, tantalum, tungsten, platinum, iridium and rhenium. The wire can also comprise a combination of more than one such material, such as an alloy of two or more materials or by providing a wire formed of one such material coated with another radiopaque material. In one preferred embodiment of the invention, for example, the wire of which the distal coil segment is formed is a tungsten wire plated with gold.

The proximal coil segment 22 is attached to the distal length 14 of the wire 11 by any suitable means. For example, if the wire 11 and the proximal coil segment are both stainless steel, they can be attached to one another by conventional welding, brazing or soldering. It can be particularly difficult to weld, braze or solder nitinol, however, and if nitinol is employed for one or both of the wire 11 and the proximal coil segment, a different means of bonding may need to be employed to get a strong connection. It has been found that a coil can be adequately secured to a nitinol wire by means of a biocompatible cementitious material, such as a polymeric bonding agent like a class 6 curable epoxy resin.

Such resins are commercially available, e.g. from Trabond and Masterbond in the United States. As illustrated in FIGS. 1 and 2, in a preferred embodiment the bond 32 connects a proximal portion of the proximal coil segment 22 to the wire 11 adjacent the proximal end of the distal segment.

Likewise, the distal coil segment 24 is attached to the distal length 14 of the wire 11 by conventional welding, brazing or soldering or by any other suitable bonding agent. In the embodiment shown in FIG. 2, the distal end of the wire 11 includes an enlarged diameter bead 50' and the distal coil segment may be bonded directly to the bead. In particular, in the embodiment of FIG. 2 a distal portion of the distal coil segment is bonded to a rearwardly facing shoulder of the bead, as indicated by the bond at 34.

In the embodiment of FIG. 1, the distal coil segment 24 is bonded to the distal length 14 of the wire 11, but it need not be not bonded directly thereto. Instead, the distal end of the guidewire 10 comprises a bead 50 which is bonded to both a distal portion of the distal coil segment and an area of the distal length 14 adjacent its distal end. The use of such beads is well known in the art, as are means for connecting the beads to core wires and helical coils.

As noted above, the proximal coil segment 22 is attached to the distal coil segment 24, but the core wire remains free-floating within the lumen of the combined coil 20. In the prior art, such coil segments are attached by conventional brazing or soldering and the junction between the two coils is also bonded to the wire extending through the lumen of the coil. For example, Samson et al. stress in U.S. Pat. No. 4,538,622 that this junction between the coil segments and the wire in the lumen should be formed into "a unitary assembly". Even where this is not expressly taught in the art, when one solders or brazes this junction, the solder or braze will tend to be wicked down into the lumen of the coil by capillary action and bond this junction to the wire.

In accordance with the present invention, the distal end of the proximal coil segment 22 is abutted against the proximal end of the distal coil segment 24 and the coil segments are bonded to one another by laser spot-welding, such as with a YAG laser or excemer laser. Equipment for laser spot welding is commercially available, such as from Leumonics. These coils could be bonded to one another within the scope of the invention by plasma welding, but it is not believed that this would work as well for some of the materials used in guidewire construction.

Although any number of turns could be welded together with such a laser, it has been found that welding as few as one or two turns of the proximal coil segment to a similar number of turns of the distal coil segment can yield a tensile pull strength at this juncture which is more than sufficient to meet the structural demands placed on the guidewire 10. In one embodiment which appears to be suitable, the coil segments 22, 24 are welded at four spots spaced about the circumference of the coil 20 but at approximately the same position along the length of the coil. Using such welds to cover about one half of the surface area of a relatively short length of eh coil (e.g. three to six turns of eh wire), has been found to yield acceptable pull strengths.

For example, with a proximal coil segment 22 formed of 0.003 inch (about 0.075 mm) 304 stainless steel wire and a distal coil segment formed of about 0.003 inch tungsten wire having a gold coating on the order of a few angstroms or less, tensile pull strengths in excess of 5 pounds have been achieved by joining only two turns of each coil segment together at the junction. As the pull strength of a stainless steel coil segment or a tungsten coil segment is frequently closer to about 1 pound, this forms a bond between the distal end of the proximal coil segment and the proximal end of the distal coil segment which is actually stronger than the rest of the coil and should be able to withstand the rigors of common use.

The advantage of the present invention over prior art designs are numerous. One advantage of this design over prior designs is that a strong bond between the proximal and distal coil segments (22 and 24, respectively) can be obtained while locking just a few turns of the wire together. In prior art designs, 10 or more turns of the two coils have to be joined together in a stiff solder or braze joint. For example, Samson et al. teach that the brazing joint taught therein should fill the interstices between the turns of the coil, making this joint particularly inflexible.

As this prevents the guidewire from bending at the joint between the two coils, the guidewire has a relatively sharp discontinuity in flexibility at this point. As explained above, this can make the guidewire more difficult to steer because it will not readily track curvature of the vessels through which it is being guided. Such a discontinuity in flexibility also makes it more difficult to track a catheter or other treatment device over the guidewire. By minimizing the number of turns of the coil segments 22, 24 which must be joined together in the present design, the stiffened section of the coil 20 can be kept to a minimum, reducing or substantially eliminating the difficulties in steering and tracking exhibited by prior art designs.

The present invention also allows the distal length 14 of the wire 11 to float freely within the lumen of the coil 20, with the wire 11 and the coil being linked together only at the distal and proximal extremities of the coil. As the present guidewire 10 is guided along a curved path, the wire 11 can move with respect to the coil 20, i.e. it can move from side to side within (or "float" with respect to) the coil. Although the gap between the wire 11 and the inner surface of the coil is not particularly large, this ability of the wire to float within the coil can dramatically increase the flexibility of the distal portion of the guidewire, making it easier to steer the guidewire through a more tortuous path.

The free-floating design of the present invention can also make it easier to guide the guidewire through a narrowing of a vessel and steer the wire beyond that narrowing. As noted above, in a design wherein the wire 11 is bonded to the coil 20 (such as in the design proposed by Samson et al.), if the guidewire 10 is passed through a narrowing of the vessel, it can be difficult to turn the wire against the frictional forces between the coils of the guidewire and the patient's tissue. With a free-floating coil in accordance with the present invention, however, the wire 11 can move with respect to the coil 20. Accordingly, when an operator turns a proximal portion of the guidewire, the distal tip of the guidewire can still be turned because the coil can absorb some torsional stress. Once the operator has properly oriented the distal tip of the guidewire to steer it along the desired course, he or she can urge the wire forward. Once the coil disengages from the narrowing of the vessel (e.g. once it clears an atheroma), it will tend to return to its original, unstressed state.

The embodiments described above and shown in FIGS. 1 and 2 only employ one relatively radiopaque distal coil segment and one less radiopaque proximal segment. It should be understood, however, that one could have a number of coils of differing materials joined together end-to-end in keeping with the concepts of the present invention.

For example, the coil 20 could include a proximal coil segment 22 and a distal coil segment 24, as described above, but also include first and second intermediate coil segments (not shown). The proximal end of the proximal coil segment could be bonded to the wire 11 as described above, the proximal end of the first intermediate coil segment could be joined to the distal end of the proximal coil segment 22, the distal end of the first intermediate coil segment could be joined to the proximal end of the second intermediate coil segment, the distal end of the second intermediate coil segment could be joined to the proximal end of the distal coil segment 24 and the distal end of the distal coil segment could be bonded to the wire 11 adjacent its distal end as described above. If one were to make the proximal and second intermediate coil segments of a less radiopaque material and the first intermediate and distal coil segments of a more radiopaque material, these differences in opacity will be visible to the operator. By making the first and second intermediate coil segments and the distal coil segment of predetermined lengths, this can provide a guidewire with a built-in ruler allowing the operator to gauge the size of a feature of the patient's tissue with an in-situ reference guide. So long as the coil remains free-floating within the lumen of the coil, the advantages of the present invention over the prior art devices will be maintained.

Figure 3:
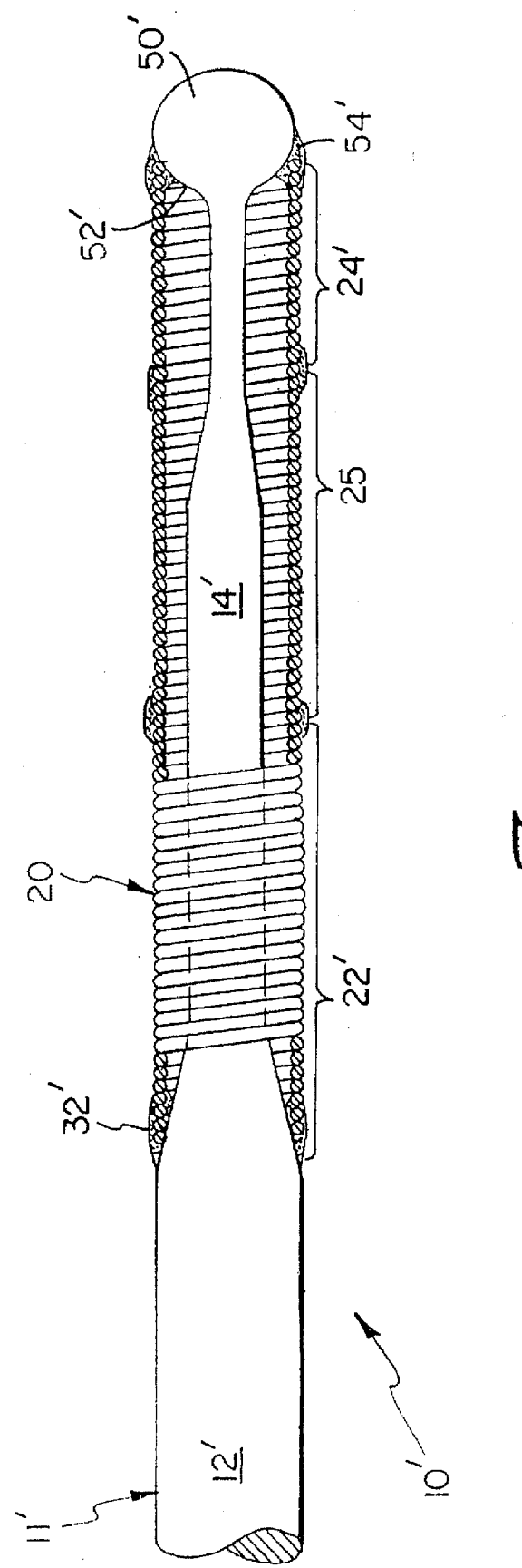
FIG. 3 is a side view in partial cross section of another alternative embodiment of a guidewire of the invention.

Alternatively, the coil may comprise three segments rather than two or four as in the above embodiments. As illustrated in FIG. 3, such a guidewire 10' may include a proximal coil segment 22', a distal coil segment 24' and an intermediate coil segment 25. In this embodiment, both the proximal segment 22' and the distal segment 24' may be made of the same material while the intermediate coil segment 25 may be made of a different material. For example, both the proximal segment 22' and the distal segment 24' may be made of a relatively radiopaque material such as those mentioned above for the distal segment 24 and the intermediate segment 25 may be made of a less radiopaque material, e.g. stainless steel or nitinol. The intermediate coil segment 25 may have a fixed, predetermined length, e.g. 3 cm.

In this embodiment, the distal end of the distal segment and the proximal end of the proximal segment are bonded to the wire 11. The distal end of the proximal segment is attached to the proximal end of the intermediate segment by laser spot welding or plasma welding and the distal end of the intermediate segment is attached to the proximal end of the distal segment in much the same manner. This construction will still provide the advantages of a coil having varying radiopacity along its length and permit the coil to float freely with respect to the wire between the proximal and distal ends of the coil.

When an operator uses the guidewire 10', the distal segment and the proximal segment will be easy to see on a fluoroscope or the like due to their radiopacity. When the guidewire has reached the desired treatment site, the intermediate segment can be positioned in the area of the treatment site, with the distal segment optimally being positioned distally of the treatment site and the proximal segment optimally being positioned proximally of the treatment site. The relatively low radiopacity of the intermediate segment will permit the operator to see the treatment site without undue interference from the guidewire. By providing the guidewire with an intermediate coil segment of a fixed, predetermined length, an operator has a built-in size reference to assist in estimating the dimensions of the tissue to be treated.

As noted above, the present invention also contemplates a method of making a guidewire. In accordance with this method, a wire 11 having proximal length 12 and a distal length 14 substantially as described above is provided, as are a proximal length of a coil formed of a less radiopaque material and a distal coil segment of a more radiopaque material. The proximal coil segment 22 is bonded to the wire 11 adjacent the proximal end of the segment 22, such as by welding, brazing or soldering or by means of a biocompatible cementitious compound, and the distal end of the proximal coil segment is attached to the proximal end of the distal coil segment by laser spot welding. The distal end of the distal coil segment is bonded to the core wire adjacent its distal end, either directly or indirectly, such as by bonding both the distal end of the distal coil segment and the distal end of the coil to a distal bead. The joint between the distal end of the distal segment 24 and the wire 11 can be formed in the same ways that the proximal end of the proximal segment 22 is attached to the wire.

These steps can be performed in a variety of different sequences, yet still arrive at much the same final structure. For example, the coil can be formed by laser spot-welding the two (or more) coil segments together apart from the wire 11. The distal length 14 of the wire can then be placed in the lumen of the coil 20 and the ends of the coil can be attached to the wire at that time. Alternatively, the coil segments 22, 24 can first be placed on the wire and bonded thereto at the ends noted above. These two coil segments can then be laser spot-welded to one another in an abutting, end-to-end relationship, as detailed above.

In accordance with an alternative embodiment of the invention, the method of the invention is used to make a guidewire having more than two coil segments. For example, in manufacturing the guidewire 10' shown in FIG. 3, the coil 20" can be formed by laser spot-welding the distal end of the proximal segment 22" to the proximal end of the intermediate segment 25 and laser spot-welding the distal end of the intermediate segment to the proximal end of the distal segment 24'.

As noted above, the intermediate segment 25 may have a fixed, predetermined length, but both the proximal and distal segments of this coil 20' may be made longer than they need to be in the final assembled guidewire 10". This coil can then be placed over the distal length 14" of the wire and the intermediate segment can be positioned at the desired point along the length of the wire. Any excess length in the coil can be trimmed by cutting a off the proximal end of the proximal segment 22" (e.g. that portion of the proximal segment which extends proximally of the distal length 14" of the wire) and/or cutting off the distal end of the distal coil segment so that it can be attached to the bead. This will permit the intermediate segment to maintain its predetermined size without imposing unnecessarily tight tolerances on the formation of the initial coil to be placed over the wire.

While a preferred embodiment of the present invention has been described, it should be understood that various changes, adaptations and modifications may be made therein without departing from the spirit of the invention and the scope of the appended claims.

What is claimed is:

1. A guidewire comprising an elongate wire having a coil extending along at least a distal length thereof, the coil comprising a distal coil segment and a proximal coil segment, the distal coil segment being more radiopaque than the proximal segment, a distal end of the distal coil segment being attached to the wire adjacent a distal end thereof and a proximal end of the proximal coil segment being attached to the wire at a location spaced proximally of the distal coil segment, a proximal end of the distal coil segment being attached to a distal end of the proximal coil segment by a weldment, the wire received within the coil floating freely with respect to the coil between the distal end of the distal coil segment and the proximal end of the proximal coil segment.

2. A guidewire comprising an elongate wire having a coil extending along at least a distal length thereof, the coil comprising two or more coil segments, one of the coil segments being more radiopaque than at least one of the other of said coil segments, the coils being generally axially aligned with one another and abutting one another in an end-to-end relationship, a distal end of the most distal coil segment being attached to the wire adjacent a distal end thereof and a proximal end of the most proximal coil segment being attached to the wire at a location spaced proximally of said distal coil segment, each end of one of said coil segments which abuts an end of another coil segment being attached thereto by a weldment, the wire being received within the coil and floating freely with respect to the coil between the distal end of the distal coil segment and the proximal end of the proximal coil segment.

3. The guidewire of claim 2 wherein the coil comprises two coil segments, the distal end of the proximal coil segment being attached to the proximal end of the distal coil segment.

4. The guidewire of claim 3 wherein the attachment between the distal coil segment and the proximal coil segment comprises a laser spot weld.

5. The guidewire of claim 3 wherein the elongate wire comprises an elongate main wire and a safety wire, the safety wire being attached adjacent a proximal end thereof to the main wire and being attached adjacent a distal end thereof to a bead, the bead being attached to the distal coil segment.

6. The guidewire of claim 3 wherein the elongate wire is integrally formed of a single piece of metal and includes a bead at its distal end.

7. The guidewire of claim 3 wherein the distal coil segment is more radiopaque than the proximal coil segment.

8. The guidewire of claim 2 wherein the coil comprises three coil segments.

9. The guidewire of claim 8 wherein the distal coil segment and the proximal coil segment are formed of a first material and an intermediate coil segment disposed between said distal and proximal coil segments is formed of a second, different material.

10. The guidewire of claim 9 wherein the second material of which intermediate coil segment is formed is less radiopaque than the first material of which the proximal and distal segments is formed.

11. The guidewire of claim 8 wherein the intermediate coil segment has a fixed, predetermined length.

12. The guidewire of claim 8 wherein the elongate wire comprises an elongate main wire and a safety wire, the safety wire being attached adjacent a proximal end thereof to the main wire and being attached adjacent a distal end thereof to a bead, the bead being attached to the distal coil segment.

13. The guidewire of claim 8 wherein the elongate wire is integrally formed of a single piece of metal and includes a bead at a distal end thereof.

14. A guidewire comprising an elongate wire having a coil extending along at least a distal length thereof, the coil comprising a radiopaque distal coil segment and a proximal coil segment which is less radiopaque than the distal coil segment, a distal end of the distal coil segment and a proximal end of the proximal coil segment each being attached to the wire at spaced-apart locations, a proximal end of the distal coil segment being attached to a distal end of the proximal coil segment by a laser spot weld, the wire received within the coil floating freely with respect to the coil between the distal end of the distal coil segment and the proximal end of the proximal coil segment.

15. The guidewire of claim 14 wherein the elongate wire comprises an elongate main wire and a safety wire, the safety wire being attached a proximal end thereof to the main wire and being attached adjacent a distal end thereof to a bead, the bead being attached to the distal coil segment.

16. The guidewire of claim 14 wherein the elongate wire is integrally formed of a single piece of metal.

17. The guidewire of claim 16 wherein the wire includes an integrally formed bead at a distal end thereof.

* * * * *